United States Patent [19]
Yokoyama et al.

[11] Patent Number: 6,046,138
[45] Date of Patent: Apr. 4, 2000

[54] INDOLE DERIVATIVES AND ROOTING INDUCERS COMPRISING THE SAME AS THE ACTIVE INGREDIENT

[75] Inventors: Mineyuki Yokoyama; Shoko Yamaguchi; Seiichi Yoshida; Okihiko Sakamoto, all of Yokohama; Kiyotaka Kojima, Tokyo, all of Japan

[73] Assignee: Shiseido Company, Ltd., Tokyo, Japan

[21] Appl. No.: 09/029,956

[22] PCT Filed: Jul. 9, 1997

[86] PCT No.: PCT/JP97/02380

§ 371 Date: Jan. 4, 1999

§ 102(e) Date: Jan. 4, 1999

[87] PCT Pub. No.: WO98/02418

PCT Pub. Date: Jan. 22, 1998

[30] Foreign Application Priority Data

Jul. 11, 1996 [JP] Japan ................................. 8-201285
Jun. 30, 1997 [JP] Japan ................................. 9-189297

[51] Int. Cl.[7] ................. A01N 43/38; C07D 209/18; C07D 487/04
[52] U.S. Cl. ................ 504/284; 548/466; 548/494
[58] Field of Search .................... 504/284; 548/466, 548/494

[56] References Cited

FOREIGN PATENT DOCUMENTS 0 256 128  2/1988  European Pat. Off. .
97/20034   6/1997  WIPO .

OTHER PUBLICATIONS

Indole–3–Ethanol Oxidase, Frank W. Percival, William K. Purves and Larry E. Vickery, Plant Physio. 51(4), pp. 739–743, 1973.

Mass Spectrometric Identification of Indole Compounds Produce by Rhizobium Strains, J. Badenoch–Jones, R.E. Summons, B. Entsch, B.G. Rolfe, C.W. Parker and D.S. Letham, Biomed. Mass Spectrom, 9(10), pp. 429–437, 1982.

Liebich et al., CA 112:194825 (1990).

*Primary Examiner*—Laura L. Stockton
*Attorney, Agent, or Firm*—Foley & Lardner

[57] ABSTRACT

An indole derivative having the formula (I) or (II) and root formation inducing agents wherein these indole derivatives are an effective ingredient:

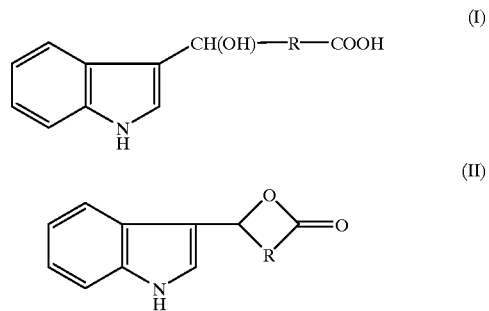

wherein, R does not exist or represents a $C_1$ to $C_4$ alkylene group.

8 Claims, 3 Drawing Sheets

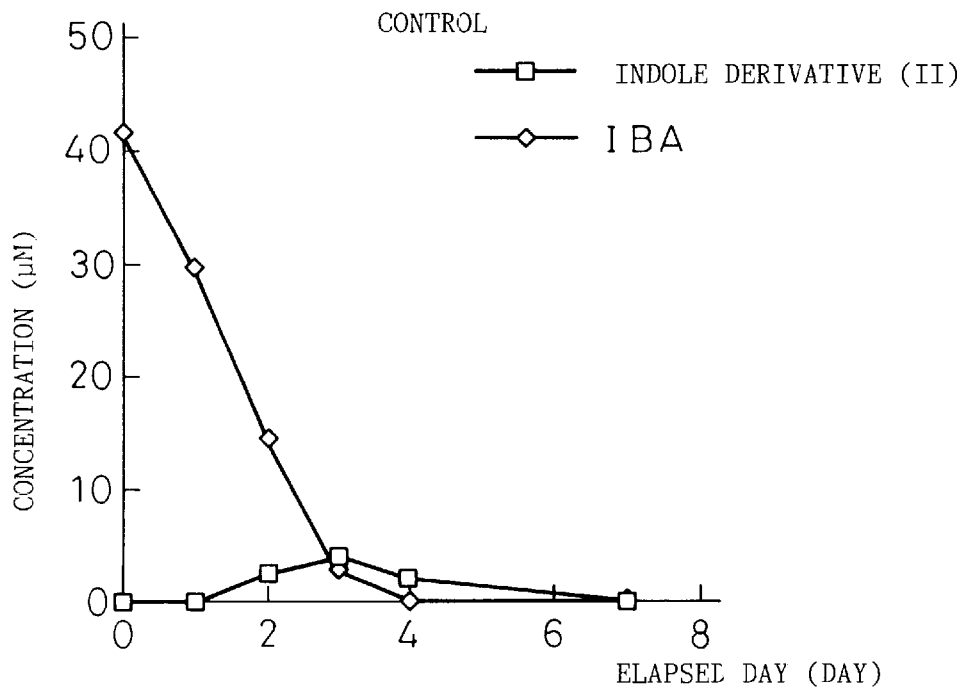
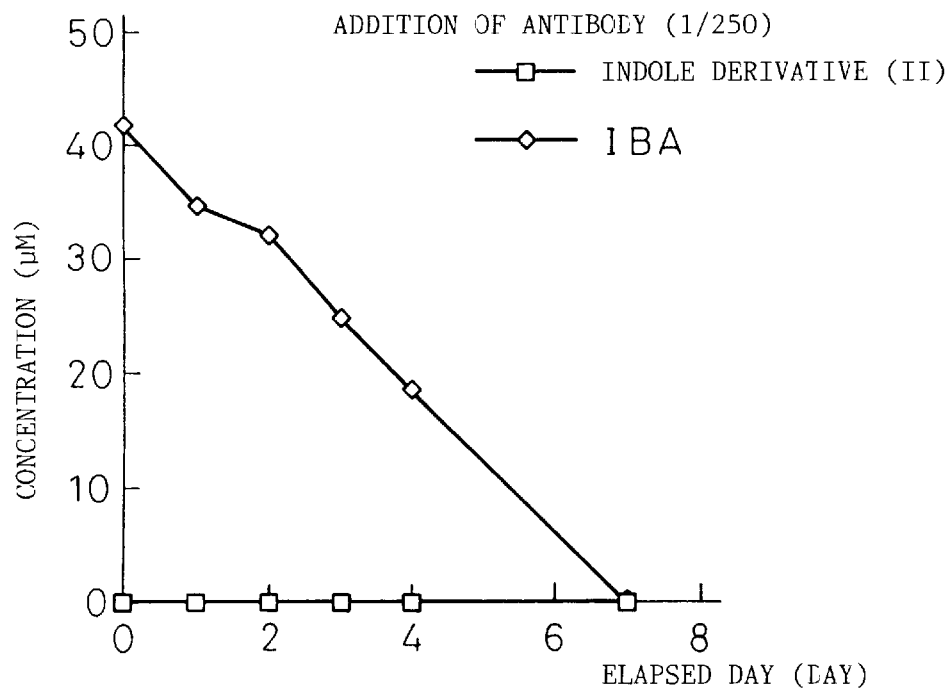

INDOLE DERIVATIVES AND ROOTING INDUCERS COMPRISING THE SAME AS THE ACTIVE INGREDIENT

This application is a 371 of PCT/JP97/02380 filed Jul. 9, 1997.

TECHNICAL FIELD

The present invention relates to an indole derivative having a specific structure and to a root formation inducing agent wherein this indole derivative is an effective ingredient.

BACKGROUND ART

When a plant is intended to proliferate by a seed, normally it is required that the seed be a pure line. This is because if a pure line seed is not used, the characters of the proliferated plant are diverse. However, there are difficulties when obtaining a pure strain seed through seed proliferation. Further, seed proliferation is limited to a plant from which a seed can be easily obtained.

Therefore, in addition to the above seed proliferation, a vegetative proliferation method, that is, the cutting method is widely used, where a part of the vegetative organs of a plant is cut off from the mother plant to be proliferated, inserted into sand or soil, to thereby form roots and shoots and form an independent plant.

There are however many plants for which the root formation is difficult even with the vegetative proliferation method (for example, pine, fir, hemlock, cedar, tea plants, Magnolia hypoleuca, liriodendron, nettle tree, chestnut tree, oak tree, hornbeam, walnut tree, myrica, etc.). At the time of using "cuttings" of these plants, it has become essential to use auxin root formation inducing agents such as Rooton (phonetic) ingredients: 1-naphthylacetoamide), Auxiberon (phonetic) ingredients: indolebutyric acid).

However, even when using auxin root formation agents, root formation of the above mentioned plants is still difficult in many cases. Therefore, the amount of them used becomes inevitably larger. The use of a large amount of a root formation inducing agent for chestnut trees etc. is feared in some cases to cause environmental pollution. Further, when a root formation agent is used, pretreatment by silver nitrate, potassium permanganate, lime water, ethanol etc. is necessary in many cases. This is also one factor the use of a root formation agent is made complicating.

DISCLOSURE OF INVENTION

Accordingly, the object of the present invention is to find a novel root formation inducing substance superior in root formation action compared with the known root formation inducing substances and capable of inducing root formation in a broad range of plants and to provide a root formation inducing agent wherein this root formation inducing substance is an effective ingredient.

In accordance with to the present invention, there is provided an indole derivative having the formula (I). Note that this indole derivative (I) is preferably one where R in the following formula (I) is an ethylene group:

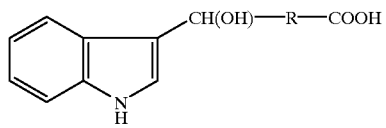

wherein R does not exist or represents a $C_1$ to $C_4$ alkylene group.

In accordance with to the present invention, there is also provided an indole derivative having the general formula (II). Note that this indole derivative (II) is preferably one in which R in the following formula (II) is an ethylene group.

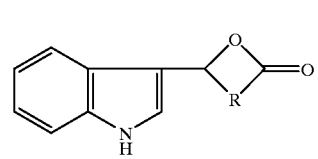

wherein R does not exist or represents a $C_1$ to $C_4$ alkylene group.

In accordance with to the present invention, there is further provided a root formation inducing agent wherein the above indole derivative (I) and/or indole derivative (II) are as an effective ingredient.

BRIEF DESCRIPTION OF DRAWINGS

The present invention will now be further explained with reference to the drawings: wherein

FIGS. 3(a) and 3(b) are drawings of the behavior of the concentrations of an indole derivative (II) and IBA in in a system comprised of an indole derivative (II) to which an antibody is added.

BEST MODE OF FOR CARRYING OUT THE INVENTION

Figure 1:
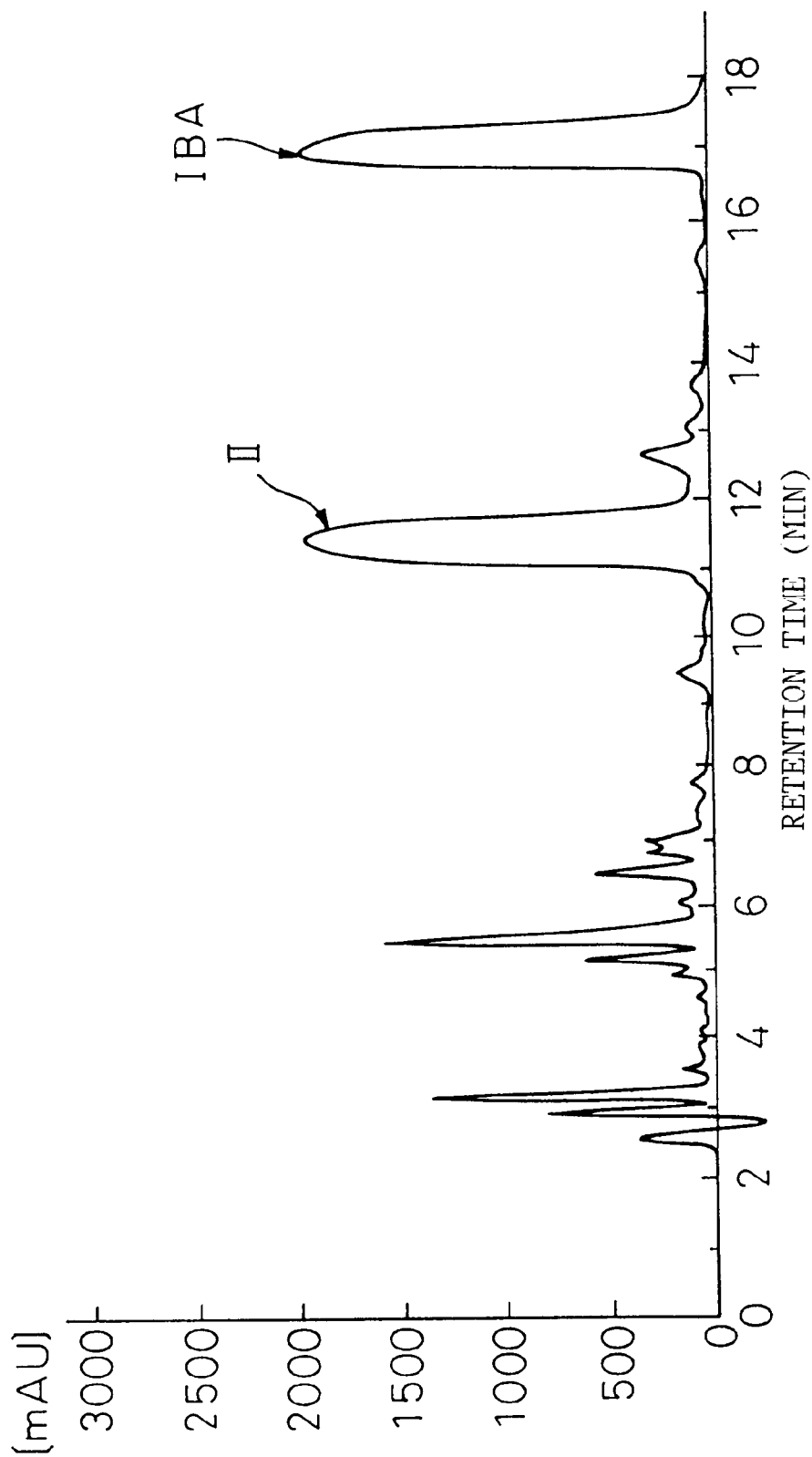
FIG. 1 is a chart of the high performance liquid chromatography for the indole derivative (II) (R=ethylene group) of the present invention.

The present inventors engaged in repeated intensive studies for achieving the above object and, as a result, found that there is a strong root formation inducing activity in an indole derivative having a lactone ring at its 3-position extracted from the root of Bupleurum falcatum L. belonging to the genus Bupleurum and found that it is possible to provide a desired root formation inducing agent by including this derivative as an effective ingredient, whereby the present invention has been completed. The present inventors further succeeded in formality an intermediate for the production of the above Indole derivative, that is, an indole derivative having a hydroxyalkyl group at its 3-position.

The mode of the practice of the present invention will now be explained.

A. Regarding Indole Derivatives According to the Present Invention

In the indole derivatives (I) and (II) according to the present invention, as the "alkylene group" R, a methylene group, ethylene group, trimethylene group, and tetramethylene group may be illustrated, but in view of the strength of the root formation inducing activity etc., the alkylene group R is preferably an ethylene group.

Note that, as explained above, even indole derivatives (I) and (II) in the case where R is not present are still included within the scope of the indole derivatives of the present invention, such a type of indole derivatives (I) and (II) of the present invention may also be sometimes treated, for convenience, as "0 number of carbon atoms of alkylene (R=0)".

At least, the indole derivatives (I) and (II) of the present invention in the case where the alkylene group R is an ethylene group and in the case where the number of carbon atoms of the alkylene group R is 0 (these indole derivatives are also sometimes called generally as "the indole derivatives of the present invention") may be produced using as raw materials the root portion of plants belonging to the genus Bupleurum, in particular, *Buolerum falcatum* L.

That is, the root of a plant belonging to the genus Buoleurum is incubated in a culture medium containing indoleacetic acid (IAA) in the case of (i) an indole derivative of the present invention where the number of carbon atoms of the alkylene group is 0 and indolebutyric acid (IBA) in the case of (ii) an indole derivative of the present invention where R is an ethylene group, extraction is carried out on the culture using an organic solvent, for example, conventional extraction with an organic solvent such as chloroform extraction, ethyl acetate extraction, phenol extraction, and the organic phase is distilled off to obtain a crude product.

This is washed and concentrated, then subject to high performance liquid chromatography (HPLC) using a column of an ODS (octadecyl silane) or other reversed phase partition column chromatography and separated and purified using, for the mobile phase, a strongly acidic solvent made by TFA etc. to obtain the desired indole derivative (II) of the present invention where the number of carbon atoms of the alkylene group R is 0 or the same R is an ethylene group. Further, the indole derivative (II) of the present invention is dissolved in a polar solvent such as ethanol, methanol, and allowed to stand so as to obtain the indole derivative (I) of the present invention.

Further, if a strongly acidic solvent is not used in the mobile phase as explained above, it is possible to easily obtain the indole derivative (I) of the present invention.

Note that it is of course possible to use other usually known separating means, if necessary, for example, ultimate filtration, gel filtration chromatography, etc. in combination.

Further, the indole derivatives of the present invention can be chemically synthesized.

That is, for example, it is also possible to ① react indole-3-carboxyaldehyde, obtained by the reaction of N,N'-dimethylformamlde with indole in the presence of phosphoryl chloride, and a haloester in the presence of zinc to produce the desired indole derivative (I) of the present invention through an indole carboxylic acid ester derivative having a hydroxyl group at its side chain 1'-position and further to acidify the indole derivative (I) of the present invention by boron trifluoride etc. to form a lactone ring and obtain the indole derivative (II) of the present invention. Further, it is also possible to ② directly oxidize indole carboxylic acid in the presence of potassium tert-butoxide or another base to produce the desired indole derivative (I) of the present invention through an indole carboxylic acid ester derivative having a hydroxyl group at its side chain 1'-position and further to acidify the indole derivative (I) of the present invention by boron trifluoride etc. to form a lactone ring and obtain the indole derivative (II) of the present invention.

The reaction processes of ① and ② are shown below:

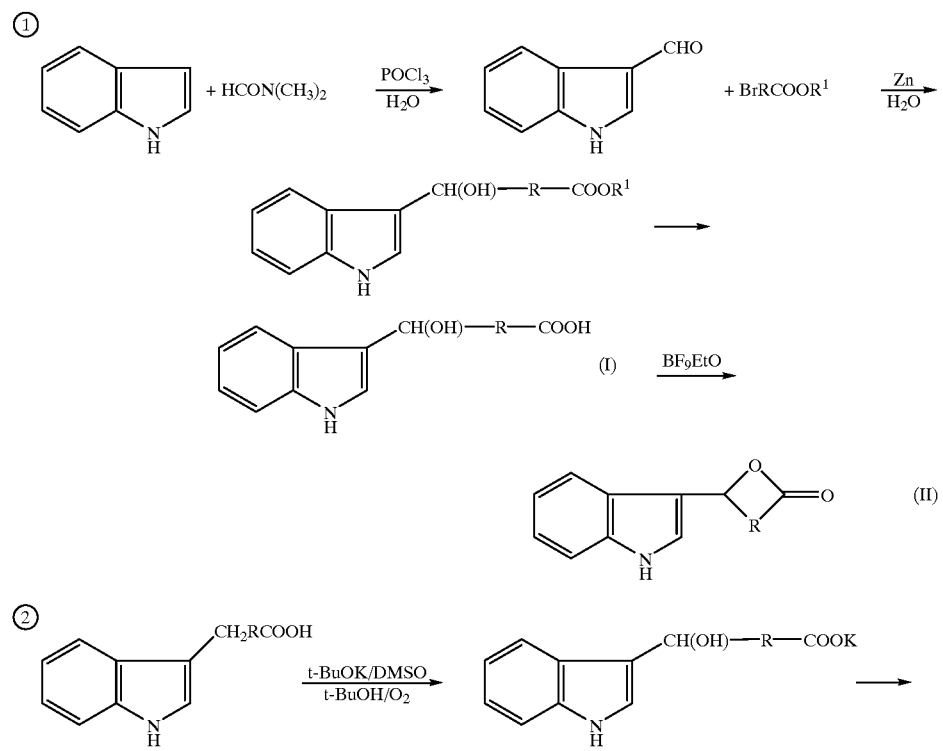

-continued

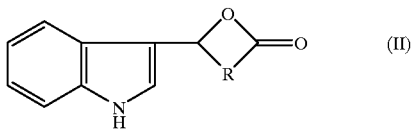

wherein, R is the same as above and $R^1$ represents a protective group.

The indole derivatives (I) and (II) of the present invention are substances which can be mutually converted to each other reversibly. If the indole derivative (I) of the present invention is placed under acidic conditions, its 3-position side chain forms a lactone ring and it converts to the indole derivative (II) of the present invention. Conversely, if the indole derivative (II) of the present invention is placed under neutral or basic conditions, its 3-position lactone ring opens and it converts to the indole derivative (I) of the present invention.

These indole derivatives (I) and (II) of the present invention both have superior root formation inducing activity.

B. Root Formation Inducing Agent of Present Invention

The root formation inducing agent of the present invention is a root formation inducing agent containing the indole derivatives (I) and/or (II) of the present invention, which are recognized as having root formation inducing activities, as an effective ingredient.

It is possible to use the indole derivatives of the present invention as they are as the root formation inducing agents of the present invention or to use them as desired agents applicable to plants, for example, liquid agents, solid agents, powder agents, emulsions, etc. No matter what type of agent, it is preferable that the indole derivatives of the present invention be stable [at the very least that the elements which the indole derivative (II) of the present invention come directly into contact with be acidic (pH of 1 to 5, preferably pH of 2 to 3)].

As long as the stability of the indole derivatives of the present invention is ensured in this way, it is possible to suitably blend in the usually known carrier components and preparation aids etc. based upon the desired type of agent. The content of the indole derivatives in this case is preferably $10^{-4}$ to $10^{-2}\%$ by weight.

As the carrier component, it is possible to use inorganic substances such as talc, clay, vermiculite, diatomous earth, kaolin, calcium carbonate, calcium hydroxide white clay, silica gel; solid carriers such as flour, starch; water; aromatic hydrocarbons such as xylene; alcohols such as ethanol, ethylene glycol; ketones such as acetone; ethers such as dioxane, tetrahydrofuran; and liquid carriers such as dimethylformamide, dimethylsulfoxide, acetonitrile. Further, it is also possible to use various buffer solutions for maintaining the pH constant.

Further, as a preparation aid, for example, it is possible to suitably formulate cationic surfactants such as alkyl sulfuric acid esters, alkyl sulfonates, alkylaryl sulfonates, dialkyl-sulfosuccinic acids; anionic surfactants such as higher aliphatic amine salts; non-ionic surfactants such as polyoxyethylene glycol alkyl ethers, polyoxyethylene glycol acyl esters, polyoxyethylene glycol polyhydric alcohol acyl esters, cellulose derivatives; thickeners such as gelatin, casein, arabia gum; extender filters; binding agents, etc.

Further, it is possible to formulate, if necessary, a plant growth regulator, for example, benzoic acid, nicotinic acid, nicotinic acid amide, pipecolic acid, etc. to an extent not impairing the desired effect of the root formation inducing agent of the present invention.

The root formation inducing agent of the present invention may be used for various plants by methods depending upon the type of the agent. For example, a powder agent may be applied to the cut of a vegetative organ of a plant for which root formation is being induced or a liquid agent may be soaked into the cut of the plant.

The type of the plant to which the root formation inducing agent of the present invention can be applied is not particularly limited. The root formation inducing agent of the present invention is effective for both dicotyledon and monocotyledon.

The root formation inducing agent of the present invention can induce the root formation of plants by being administered to plants for which known root formation inducing agents are ineffective.

EXAMPLES

The present invention will now be described in more detail, by the following Examples, but the technical scope of the present invention is of course not limited to these Examples.

Production Examples (1) Production of Indole Derivative of Present Invention Where R is Ethylene Group 8 g of the root of minced *Bupleurum falcatum* L. was cultured at 23° C. for 24 hours in a sterilized B5 medium ($KNO_3$ (2500 mg/L), $(NH_4)_2SO_4$ (134 mg/L), $NH_2PO_4.H_2O$ (150 mg/L), $CaCl_2.2H_2O$ (150 mg/L), $MgSO_4.7H_2O$ (185 mg/L), $FeSO_4.7H_2O$ (27.8 mg/L), $Na_2EDTA$ (37.3 mg/L), $MnSO_4.H_2O$ (10 mg/L), $ZnSO_4.7H_2O$ (2.0 mg/L), $H_3BO_3$ (3.0 mg/L), $CuSO_4.5H_2O$ (0.025 mg/L), $Na_2MoO_2.2H_2O$ (0.25 mg/L), Kl (0.75 mg/L), $CoCl_2.6H_2O$ (0.025 mg/L), myoinositol (100 mg/L), thiamine hydrochloride (10 mg/L), pyridoxlne hydrochloride (1 mg/L), nicotinic acid (1 mg/L): 400 ml each in 30 1-liter flasks) to which 8 ppm of indolebutyric acid (IBA) was added.

After the end of the culture, the root of *Buoleurum falcatum* L. was filtered out and removed from the medium, and the filtrate obtained was extracted with chloroform.

The organic layer was then treated under vacuum to distill off the solvent and to obtain the crude product.

Next, this was separated and purified by high performance liquid chromatography (column: CAPCELLPAK C18, 10 mmφ×250 mm, solvent: 70% water, 30% acetonitrile (including 0.1% TFA), detection: UV 214 nm). As a result, the peak of the indole derivative (II) of the present invention appeared at 11.5 minutes or so. This portion was separated.

As a result, 12 mg of the indole derivative (II) of the present invention was obtained (Note: the alkylene group R is an ethylene group).

Further, 2 mg of the indole derivative (II) of the present invention thus obtained was taken. This was dissolved in 2 ml of methanol. The solution was agitated at room temperature for 7 days, then the methanol was distilled off by an evaporator.

As a result, the indole derivative (I) of the present invention where the alkylene group R is an ethylene group was obtained.

The structure of the indole derivative (II) of the present invention (Note: R=ethylene group) obtained in the above Production Example was analyzed.

That is, the indole derivative (II) of the present invention was recognized as having 5-member ring lactone (1750 cm$^{-1}$) from its infrared absorption spectrum (IR spectrum) and was recognized as having signals in its $^1$H nuclear magnetic resonance spectrum ($^1$HNMR (400 MHz, CD$_3$OD, δ)) and $^{13}$C nuclear magnetic resonance spectrum ($^{13}$CNMR (100 MHz, CD$_3$OD, δc)) based on one hydroxyl group (δ5.89 (dd, J=7.0, 8.3), δc79.2), two methylene side chains (δ2.60, 2.75 (both m), 2.73 (m), δc30.4, 29.5), carbonyl (δc180.3), and an indole ring ((δ7.04 (dd, J=7.0, 7.8), δc119.9), (δ7.14 (dd, J=8.3, 7.0), δc122.5), (δ7.33(s), δc124.2), (δ7.37(d,J=7.3), δc112.6), (δ7.59 (d,J=7.8), δc120.1), δc115.6, 127.2, 138.5). Further, by a comparative study of the NMR data with indolebutyric acid (IBA) and analysis of the 2-dimensional NMR spectrum (HHCOSY, HSQC, HMBC), the chemical structure of a lactone ring was deduced. Further, by a comparative study of the NMR data with an open ring form (i.e., indole derivative (I) of the present invention) obtained by allowing to stand in a polar solvent, the fact that a 1'-position proton signal shifts in a magnetic field from (δ4.53 (t-like, J=6.3)) to δ5.89 and that an indole derivative of the same data as above was obtained again by separation 10 and refinement of the above open ring form (i.e., indole derivative (I) of the present invention) in an acidic solvent gave support to the assertion that the chemical structures of the indole derivatives (I) and (II) of the present invention (i.e., R=ethylene group) were the above structures.

Further, in the pos. FAB-MS spectrum of the indole derivative (II) of the present invention, a quasi molecular ion peak based on (M+H)$^+$ was recognized at m/z 202. Further, in the neg. FAB-MS spectrum as well, results supporting the above structure (m/z 200 (M−H)) were obtained. From this, it became clear that the structure of the indole derivative (II) of the present invention is as described above.

Further, the structure of the indole derivative (I) (i.e, R=ethylene group) of the present invention obtained in the above Production Example was analyzed.

That is, the indole derivative (I) of the present invention was recognized as having hydroxyl groups (3400, 3200 cm$^{-1}$) and carbonyl (1720 cm$^{-1}$) from its infrared absorption spectrum (IR spectrum). Further, it was recognized as having signals in its $^1$H nuclear magnetic resonance spectrum ($^1$HNMR (400 MHz, CD$_3$OD, δ)) and $^{13}$C nuclear magnetic resonance spectrum ($^{13}$CNMR (100 MHz, CD$_3$OD, δc)) based on one primary hydroxyl group (δ4.53 (t-like, J=6.3), δc78.3), two methylene side chains (δ2.31 (m), δc31.7, 52.13, 2.31 (both m), δ32.5), carbonyl (δc177.3), and an indole ring ((δ6.99 (dd, J=7.0, 8.0), δc120.7), (δ7.09 (dd, J=7.0, 8.5), δc123.4), (δ7.17(s), δc124.2), (δ7.34(d,J=8.5), δc113.2), (δ7.65 (d,J=8.0), δc121.2), δc115.6, 127.2, 138.6).

Further, by a comparative study of the NMR data with IBA and analysis of the 2-dimensional NMR spectrum (HHCOSY, HSQC, HMBC), it became clear that the indole derivative (I) of the present invention with the hydroxyl group bonded to the indole ring side chain 1' of the IBA has the above structure.

(2) Production of Indole Derivative of Present Invention Having R=0

4001 ml of the above B5 medium in a 1-liter flask was sterilized in an autoclave, then 2.6 ml of 2000 μg/ml Indoleacetic acid (IAA) sterilized by filtration was added. Fifty of these were prepared.

8 g of minced *Bupleurum falcatum* L. was added into each of these flasks and shake-cultured at 23° C. for 2 days. After the culture, the root of *Bupleurum falcatum* L. was removed from the system by filter paper and the medium extracted by ethyl acetate. After the extraction, the ethyl acetate was dried to a solid under a vacuum. The solid product was dissolved in methanol, then separated and purified by high performance liquid chromatography (HPLC).

Note that the separation conditions in the HPLC are the same as when separating and purifying the indole derivative (II) (i.e., R is ethylene group) in the above Production Example (1). The peak eluted at about 8.3 minutes was taken and dried to a solid under a vacuum. By this operation, it was possible to obtain approximately 1 mg of an indole derivative (II) (R=0).

Figure 2:
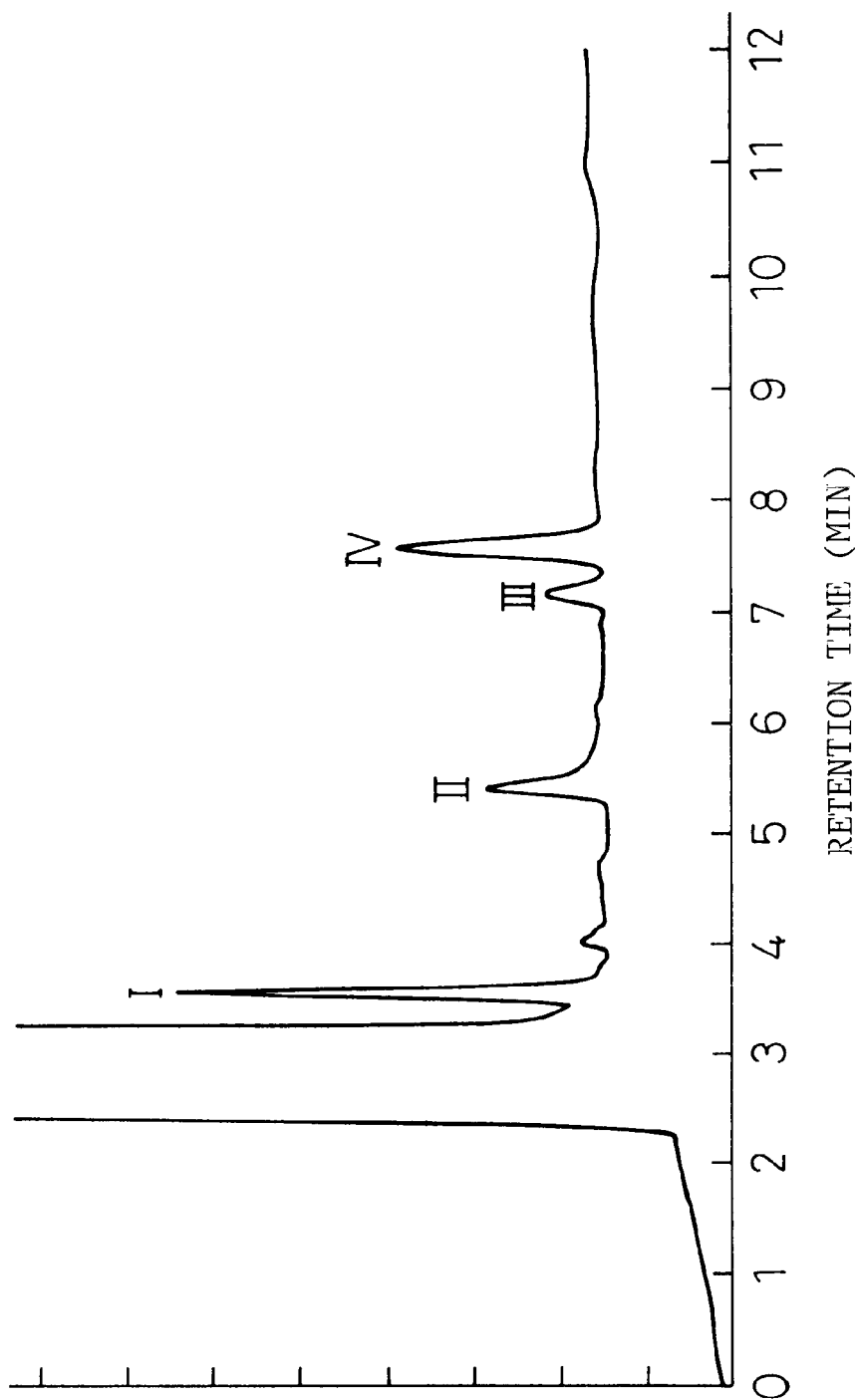
FIG. 2 is a chart of the high performance liquid chromatography for the indole derivative (II) (R=0) of the present invention.

A chart obtained by this HPLC is shown in FIG. 2 (where this chart was eluted at a flow rate of 1 ml/min using an analytical column for confirmation use (4.5 mmφ×250 mm). The peak II in the figure is the peak corresponding to the desired indole derivative (I) (R=0))

Test Examples: Study of Root Formation inducing Activity (1) Root Formation Test in *Bupleurum Falcatum* L.

Test Method

Three 100 ml flasks in which 30 ml of B5 medium (Note: components as described above and 1% by weight of sucrose is contained) was inserted and to which 0.24 ml of 1000 ppm IBA dissolved in ethanol or the indole derivative (II) (i.e., R=ethylene group) of the present invention produced in the above Production Examples was added were each prepared. Into each of these flasks, 0.2 g of the incubated root of *Bupleurum falcatum* L. was inplanted. These were shake-cultured at 23° C. and the extent of the root formation studied.

Test Results

As a result, on 8th day of the shake-culture, root formation was observed in two of the experimental regions of the indole derivative (II) of the present invention. On 9th day, root formation was observed in all of the experimental regions of the IBA and the remaining one of the experimental regions of the indole derivative (II) (i.e., R=ethylene group) of the present invention.

After this as well, the number of roots continued to increase. in 2 weeks of the shake-culure, about the same degree of dense root formation was observed over substantially all of the flasks in all experimental regions.

Next, an example using a plant for which root formation is generally difficult as will now be explained. As explained in the section on the prior art, a cutting of a plant for which root formation is generally difficult is ordinarily drastically pretreated using a large amount of a conventional root formation agent or using silver nitrate etc. Therefore, the serious problem of pollution of the environment has been caused.

(2) Root Formation Test (1) in Fragrant Olive

Small branches of fragrant olive were cut off. Fifteen each were immersed in the above B5 medium not containing sucrose (used as the control. The following experimental regions all being dissolved in the B5 medium) in the test region ①, a solution of 20 μg/ml of IBA in ②, 20 μg/ml of the Indole derivative (II) (i.e., R=ethylene group) in ③, and 10 μg/ml of TBA+10 μg/ml of the indole derivative (II) (i.e., R=ethylene group) and placed in a dark room of 25° C. for 3 days. Next, the samples were transplanted to vermiculite and cultured in an incubator for 2.5 months (cycle of 12 hours Light and 12 hours dark, 25° C.).

As a result, all of the samples withered in the test region ①. In ②, just five samples remained without withering. Of these, two formed roots. In ③, 11 samples remained without withering. Of these, eight formed roots. In ④, nine remained without withering. Of these, five formed roots.

(3) Root Formation Test (2) in Fragrant Olive

As a control, the same test as in Example 2 was carried out except for using water in place of the B5 medium. As a result, all samples withered in the test region ①. In ②, four remained alive. Of these, two formed roots. In ③, 12 remained without withering. At the time of the end of the test, nine formed roots. In ④, eight remained alive. Four formed roots.

(4) Root Formation Test in Walnut Tree

Small branches of a walnut tree were cut off and the same root formation test as in the above Test Example (2) was carried out. As a result, in the test region ①, all withered. In ② as well, all withered. In ③, Just three remained without withering. Two formed roots. In ④, five remained without withering. Of these, two formed roots.

From these results, it became clear that a root formation inducing activity at least equal to that of IBA was observed in *Bupleurum falcatum* L. with the indole derivative (II) (i.e., R=ethylene group) of the present invention. Further, even in systems where it was said that root formation was difficult in cuttings in the past, it became clear that the indole derivative (II) (i.e., R=ethylene group) of the present invention clearly induces and promotes root formation.

Therefore, the usefulness of the indole derivative (II) (i.e., R=ethylene group) of the present invention as a root formation inducing ingredient became clear and the usefulness of the root formation inducing agent of the present invention having the indole derivative (II) of the present invention as an effective ingredient became clear.

(5) Root Formation Inducing Test in Indole Derivative (I) of Present Invention

To evaluate the root formation inducing effect of the indole derivative (I) (i.e., R=ethylene group), the same test was performed on fragrant olive as in the above Test Example (2) (Note: the indole derivative (i.e., R=ethylene group) of the present invention obtained in the above Production Example (1) was used instead of the condole derivative (II)). in the test, in the test region ①, one sample remained alive, but at the end of the test, it had still not formed roots. In ②, of the four samples which remained without withering, two formed roots. In ③, 10 samples remained without withering. Of these, six formed roots. In ④, eight remained alive. Four formed roots.

Therefore, the usefulness of the indole derivative (I) (i.e., R=ethylene group) of the present invention as a root formation inducing ingredient became clear and the usefulness of the root formation inducing agent of the present invention having the indole derivative (I) of the present invention as an effective ingredient became clear (6) Test of Interference in Root Formation Action of Indole Derivative (II) of Present Invention by IBA To show whether the indole derivative (II) of the present invention is essential even with the action of IBA at the time of root formation, an interference test was performed using an antibody For the indole derivative (II) below.

① Production of Antibody for Indole Derivative (II) of Present Invention

First, the indole derivative (II) (i.e., R=ethylene group) of the present invention, obtained in the above Production Example (1), was reacted with poly-L-lysine (i.e., hapten) to combine them and cause antigenation.

For the immunized animals, domestic rabbits (healthy JW strain) were used. 0.5 mg of the antigen each was administered subcutaneously every 2 weeks for a total of 10 times along with an adjuvant (FCA).

After the end of the immunization, the serum of the immunized animals was separated, the immunoglobulins were separated from the serum, and the desired clonal antibody for the indole derivative (II) [R=ethylene group] of the present invention was obtained as antiserum. Note that in the immunized animals, whether or not the desired antibody is being produced or not was confirmed by the ELISA method.

② Interference Test 30 ml of the above B5 medium (containing 1% by weight of sucrose) was placed in a 100 ml flask and sterilized using an autoclave. To this was added 240 μl of 1000 μg/ml IBA dissolved in ethanol or the same amount of ITA and 120 μl of serum containing an antibody for an indole derivative (II) [R=ethylene group) obtained in the above ①. Three flasks each were prepared. Into each of these flasks, 0.2 g of the cultured root of *Bupleurum falcatum* L. was inplanted and shake-cultured at 23° C. At suitable times, the contents of the IBA and the indole derivative (II) (i.e., R=ethylene group) in the medium were measured. The culture was stopped after 2 weeks and the state of root formation was confirmed.

As a result, as shown in FIG. 3 (FIG. 3(a) shows a system where no antibody was added and 3(b) shows a system where an antibody was added. The vertical axis shows the amount of indole derivative (II) (i.e., R=ethylene group) or IBA), when cultured by IBA, an indole derivative (II) (i.e., R=ethylene group) was detected in the culture solution. This was deduced to be because part of the indole derivative (II) (i.e., R=ethylene group) converted from IBA has leaked into the medium (FIG. 3(a)).

On the other hand, in a flask of a test zone to which an antibody to the indole derivative (II) (i.e., R=ethylene group) was simultaneously added, no indole derivative (II) was detected at all. Further, with this system, consumption of TBA became remarkably slow (FIG. 3(b)).

Further, a look at the state of the root formation after two weeks shows that while root formation was normally observed in the control (just IBA added), almost no root formation was observed in the test zone to which an antibody to the indole derivative (II) (i.e., R=ethylene group) was added.

In this way, at least in *Bupleurum falcatum* L., it was strongly suggested that the conversion of the IBA to an indole derivative (II) (i.e., R=ethylene group) is inherently important when IBA acts in its root formation.

INDUSTRIAL APPLICABILITY

According to the present invention, an indole derivative having a powerful root formation inducing action is obtained and a root formation inducing agent having this indole derivative having a powerful root formation inducing action as an effective ingredient is provided.

We claim:

1. An indole derivative having the following formula (I):

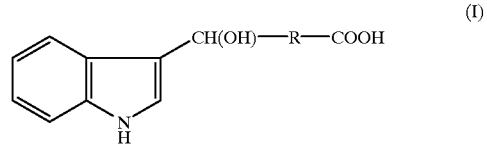

wherein R does not exist or represents a $C_1$ to $C_4$ alkylene group, provided that indole-3-propanoic acid and indole-3-glycolic acid are excluded.

2. An indole derivative claimed in claim 1, wherein the alkylene group R is an ethylene group.

3. An indole derivative having the formula (II):

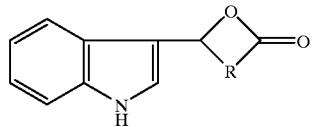

(II)

wherein, R does not exist or represents a $C_1$ to $C_4$ alkylene group.

4. An indole derivative as claimed in claim 3, wherein the alkylene group R is an ethylene group.

5. A method for inducing root formation comprising applying to a plant an indole derivative (I) according to claim 1 in an effective amount.

6. A method for inducing root formation comprising applying to a plant an indole derivative (II) according to claim 3 in an effective amount.

7. A method for inducing root formation comprising applying to a plant an indole derivative (I) according to claim 2 in an effective amount.

8. A method for inducing root formation comprising applying to a plant an indole derivative (II) according to claim 4 in an effective amount.

* * * * *